US012651668B2

(12) United States Patent
Karimi et al.

(10) Patent No.: US 12,651,668 B2
(45) Date of Patent: Jun. 9, 2026

(54) ENVIRONMENTAL EXPOSURE AND LUNG HEALTH MONITORING DEVICE

(71) Applicant: THE UAB RESEARCH FOUNDATION, Birmingham, AL (US)

(72) Inventors: Maryam Karimi, Birmingham, AL (US); Rouzbeh Ross Nazari, Birmingham, AL (US); S. Abdollah Mirbozorgi, Irondale, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 272 days.

(21) Appl. No.: 18/328,378

(22) Filed: Jun. 2, 2023

(65) Prior Publication Data
US 2023/0395257 A1 Dec. 7, 2023

Related U.S. Application Data

(60) Provisional application No. 63/348,204, filed on Jun. 2, 2022.

(51) Int. Cl.
G16H 50/20 (2018.01)
G16H 40/60 (2018.01)

(52) U.S. Cl.
CPC ............. G16H 50/20 (2018.01); G16H 40/60 (2018.01)

(58) Field of Classification Search
CPC ............................... G16H 50/20; G16H 40/60
USPC ........................................................ 705/2–3
See application file for complete search history.

(56) References Cited

U.S. PATENT DOCUMENTS

| | | | | |
|---|---|---|---|---|
| 11,490,852 B1 * | 11/2022 | Kurani | ................... | A61B 5/411 |
| 11,761,939 B1 * | 9/2023 | Cridge | .............. | G01N 33/0062 |
| | | | | 73/31.02 |
| 12,068,076 B1 * | 8/2024 | Alexopoulos | .......... | G16H 40/20 |
| 2011/0055720 A1 * | 3/2011 | Potter | ................... | G06F 3/0481 |
| | | | | 709/217 |
| 2013/0231574 A1 * | 9/2013 | Tran | ..................... | A61B 5/0022 |
| | | | | 600/509 |
| 2015/0309535 A1 * | 10/2015 | Connor | ................ | A61B 5/1477 |
| | | | | 361/679.03 |
| 2016/0282151 A1 * | 9/2016 | Kursula | ............. | G01N 33/0044 |
| 2016/0349790 A1 * | 12/2016 | Connor | .................. | G06F 3/017 |
| 2017/0085773 A1 * | 3/2017 | Hirabayashi | ......... | H04N 23/667 |
| 2017/0323550 A1 * | 11/2017 | Patil | ........................ | G08B 5/22 |
| 2017/0351221 A1 * | 12/2017 | Balti | .................. | G01N 33/0037 |
| 2019/0012895 A1 * | 1/2019 | Myers | ................ | G08B 21/0446 |

(Continued)

*Primary Examiner* — Michael Tomaszewski

(74) *Attorney, Agent, or Firm* — Thomas | Horstemeyer, LLP

(57) ABSTRACT

The present disclosure presents wearable sensor apparatuses, systems, and related methods. One such apparatus is in the form of a wearable sensor device that comprises a processor and a plurality of gas sensors integrated on the wearable sensor device, in which the gas sensors measure an amount of $NO_2$, $SO_2$, and $O_3$ present in ambient air. The wearable sensor device further comprises a peak flow meter sensor integrated on the wearable sensor device; a temperature sensor integrated on the wearable sensor device; a GPS sensor integrated on the wearable sensor device; one or more transceivers integrated on the wearable sensor device; and an electronic display, wherein the processor is coupled to the electronic display and is operable to display sensor data measured from the wearable sensor device.

20 Claims, 16 Drawing Sheets

(56)  References Cited

U.S. PATENT DOCUMENTS

| | | | |
|---|---|---|---|
| 2020/0237947 A1* | 7/2020 | Brown | A61L 9/015 |
| 2021/0134319 A1* | 5/2021 | Vatanparvar | A61B 5/0823 |
| 2021/0166793 A1* | 6/2021 | Mobarakeh | G06Q 30/0201 |
| 2022/0052836 A1* | 2/2022 | Kosecoff | H04L 9/3239 |
| 2023/0064273 A1* | 3/2023 | Tadele | A61B 5/6898 |
| 2023/0395257 A1* | 12/2023 | Karimi | G16H 20/10 |

* cited by examiner

100

110

DISPLAY
115

AIR VENT

TEMPERATURE
SENSOR PAD

BUTTON
CONTROLS 120     130     140

150     160     170

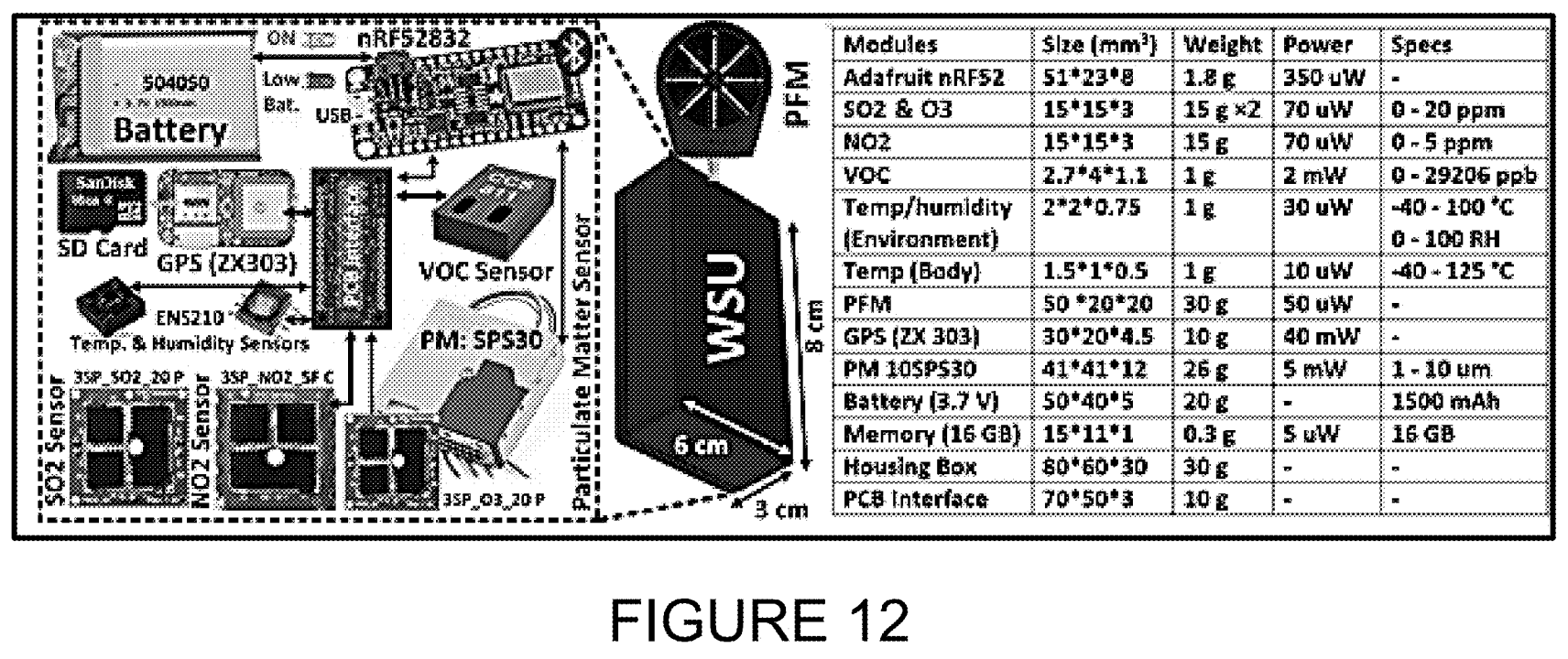

| Modules | Size (mm³) | Weight | Power | Specs |
|---|---|---|---|---|
| Adafruit nRF52 | 51*23*8 | 1.8 g | 350 uW | - |
| SO2 & O3 | 15*15*3 | 15 g ×2 | 70 uW | 0 - 20 ppm |
| NO2 | 15*15*3 | 15 g | 70 uW | 0 - 5 ppm |
| VOC | 2.7*4*1.1 | 1 g | 2 mW | 0 - 29206 ppb |
| Temp/humidity (Environment) | 2*2*0.75 | 1 g | 30 uW | -40 - 100 °C 0 - 100 RH |
| Temp (Body) | 1.5*1*0.5 | 1 g | 10 uW | -40 - 125 °C |
| PFM | 50*20*20 | 30 g | 50 uW | - |
| GPS (ZX 303) | 30*20*4.5 | 10 g | 40 mW | - |
| PM 10SPS30 | 41*41*12 | 26 g | 5 mW | 1 - 10 um |
| Battery (3.7 V) | 50*40*5 | 20 g | - | 1500 mAh |
| Memory (16 GB) | 15*11*1 | 0.3 g | 5 uW | 16 GB |
| Housing Box | 80*60*30 | 30 g | - | - |
| PCB Interface | 70*50*3 | 10 g | - | - |

FIGURE 12

ENVIRONMENTAL EXPOSURE AND LUNG HEALTH MONITORING DEVICE

CROSS-REFERENCE TO RELATED APPLICATION

This application claims priority to U.S. provisional application entitled, "Environmental Exposure and Lung Health Monitoring Device," having Ser. No. 63/348,204, filed Jun. 2, 2022, which is entirely incorporated herein by reference.

BACKGROUND

Urbanization and globalization have played a vital role in raising global air pollution. According to the United States Environmental Protection Agency (EPA) report of 2020, approximately 68 million tons of air pollutants were emitted into the atmosphere in the United States. Increase in emission leads to a significantly higher health risk for individuals with severe chronic health diseases such as Asthma and chronic obstructive pulmonary disease (COPD).

Despite substantial research, the current public health system faces key challenges in finding a potential trigger of respiratory symptoms caused by pollutants in the surrounding environment. The local and federal organizations have set up several expensive stationary air quality monitoring stations with real-time data broadcasting systems for citizens. However, these stations have low spatial resolution since a small number of them are available in cities. Given that it is crucial to monitor indoor air quality as humans spend ~90% of their time indoors, it is necessary to monitor a real-time stochastic environment and to provide notifications or alerts to avoid a particular path or environment that is subject to poor air quality.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 12 shows specifications of an exemplary SCHMT device in accordance with various embodiments of the present disclosure.

DETAILED DESCRIPTION

The present disclosure describes various embodiments of systems, apparatuses, and methods to measure a lung's performance of a user along with the surrounding ambient environment parameters at a given instant of time.

With the modern digitization revolution and IoT Industrial 4.0 technology, the conventional methods for measuring physiological parameters have been eliminated, and modern technologies have enabled an interconnected world where people are connected with all their wearable or non-wearable gadgets. Over time, numerous wearable devices have been developed in the healthcare system for monitoring the patient's health status. These new emerging devices include advanced biomedical sensors, miniaturized intelligent processors, and wireless data transmission technology. Wearable devices for air quality monitoring systems have been developed in commercial and non-commercial sectors. However, there are some limitations in commercial products such as size, cost, and product features. For instance, the Tzoa wearable sensor only monitors ambient light, air quality (PM), atmospheric pressure, temperature, and humidity. In addition, the utilization of commercial devices in the healthcare system is quite limited because of size constraints. While in the non-commercial sector, multiple types of wearable devices are used in clinical studies and by researchers to measure different air pollutants, temperatures, and humidity. Currently, there are no such devices that can measure the lung's performance along with the surrounding ambient environment parameters at a given instant of time. Moreover, self-assessment of lung performance plays a vital role in halting the chronic disease and preventing its progression to severe disease.

Thus, the present disclosure presents a new air monitoring device called the Smart Chronic Health Monitoring Tool (SCHMT). In accordance with various embodiments, an exemplary SCHMT device is a novel wearable device that measures various significant air pollutants (usually contributing to chronic diseases) and examines lung performance (using a peak flow meter (PFM)), simultaneously. In various embodiments, the SCHMT is a compact chest or waist wearable device (e.g., via a clip or cord/necklace) that can improve patients' lifestyles with severe chronic diseases. The SCHMT will also help in various clinical studies for evaluating the potential trigger of chronic attacks by hazardous environmental exposure.

Figure 1A:
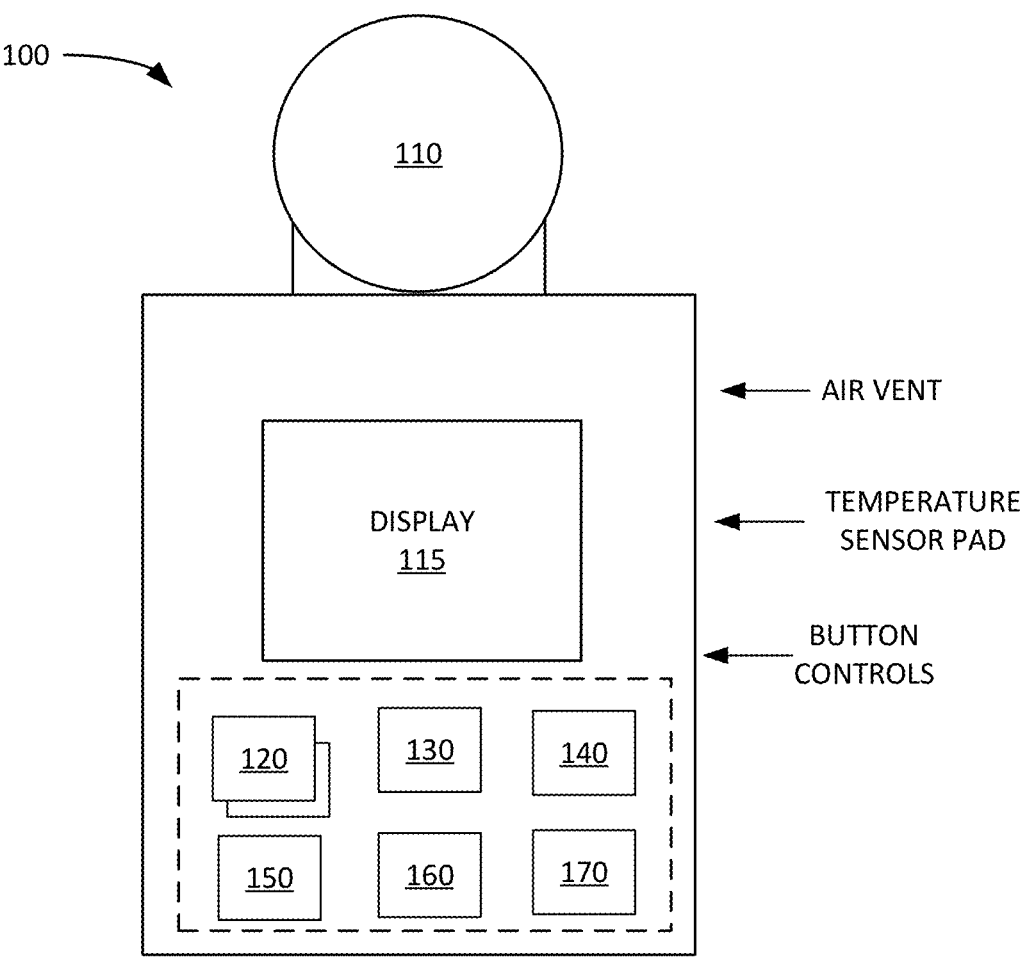
FIG. 1A shows a block diagram of an exemplary Smart Chronic Health Monitoring Tool (SCHMT) device in accordance with various embodiments of the present disclosure.

FIG. 1A shows a block diagram of an exemplary SCHMT device 110 that contains a peak flow meter 110, gas sensors 120 (e.g., $NO_2$, $SO_2$, $O_3$), a particulate matter sensor 130

(e.g., PM0.5-10), a temperature sensor 140, an environment temperature sensor 150, a global positioning sensor (GPS) location unit 160, and a microprocessor component 170 that is coupled to the various sensor units. Measurements obtained by the sensors can be displayed on an electronic display 115 of the SCHMT device, along with alerts, notifications, or other types of information. In various embodiments, an exemplary SCHMT device 100 can be equipped to detect various air pollutants, including, but not limited to, volatile organic compounds (VOCs), particulate matter (1, 0.5, 5, and carbon monoxide, nitrogen dioxide, ozone, sulfur dioxide, etc.

Figure 1B:
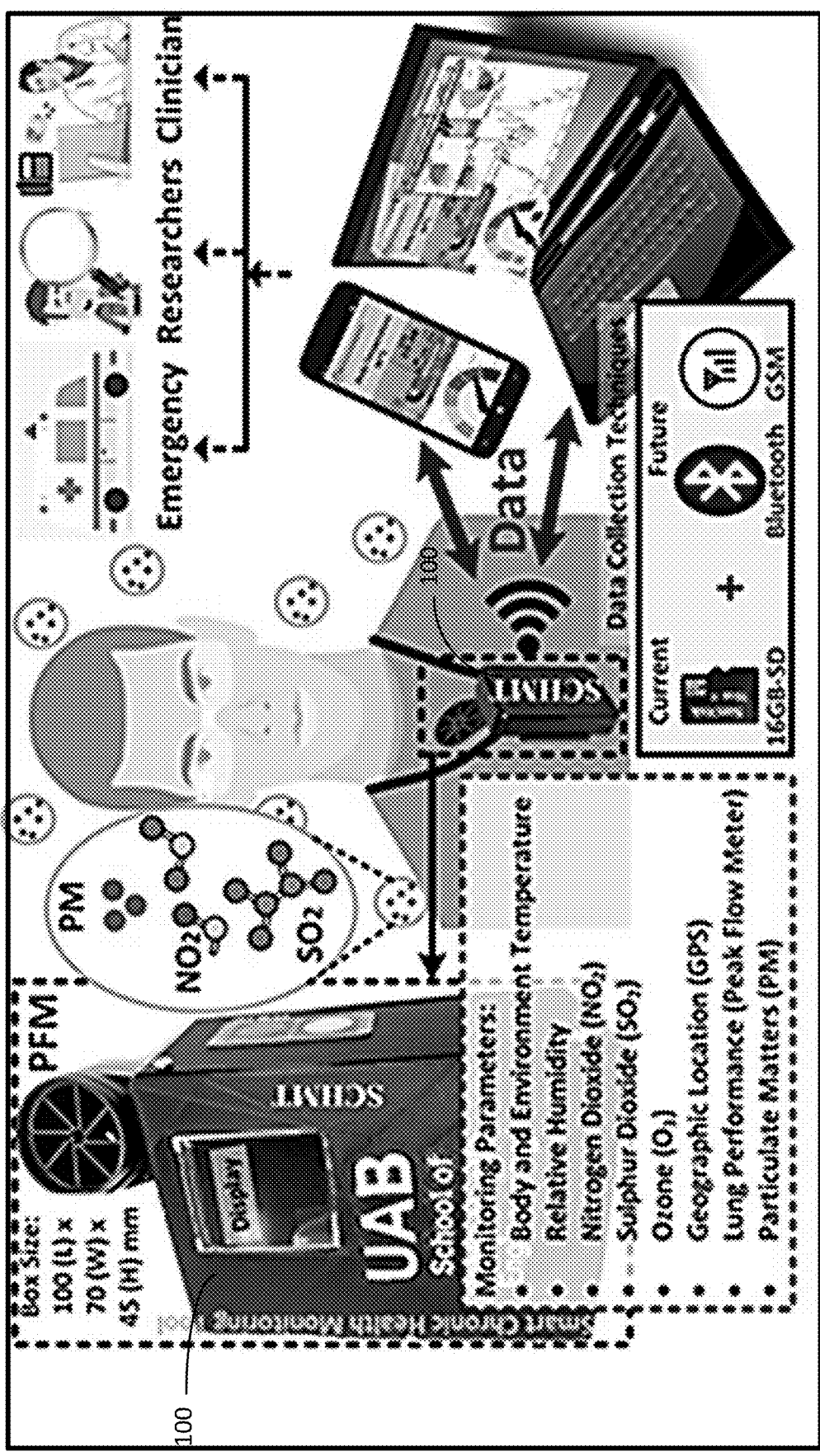
FIG. 1B shows a schematic of an exemplary system of the present disclosure that features the SCHMT device of FIG. 1A.
Figure 2:
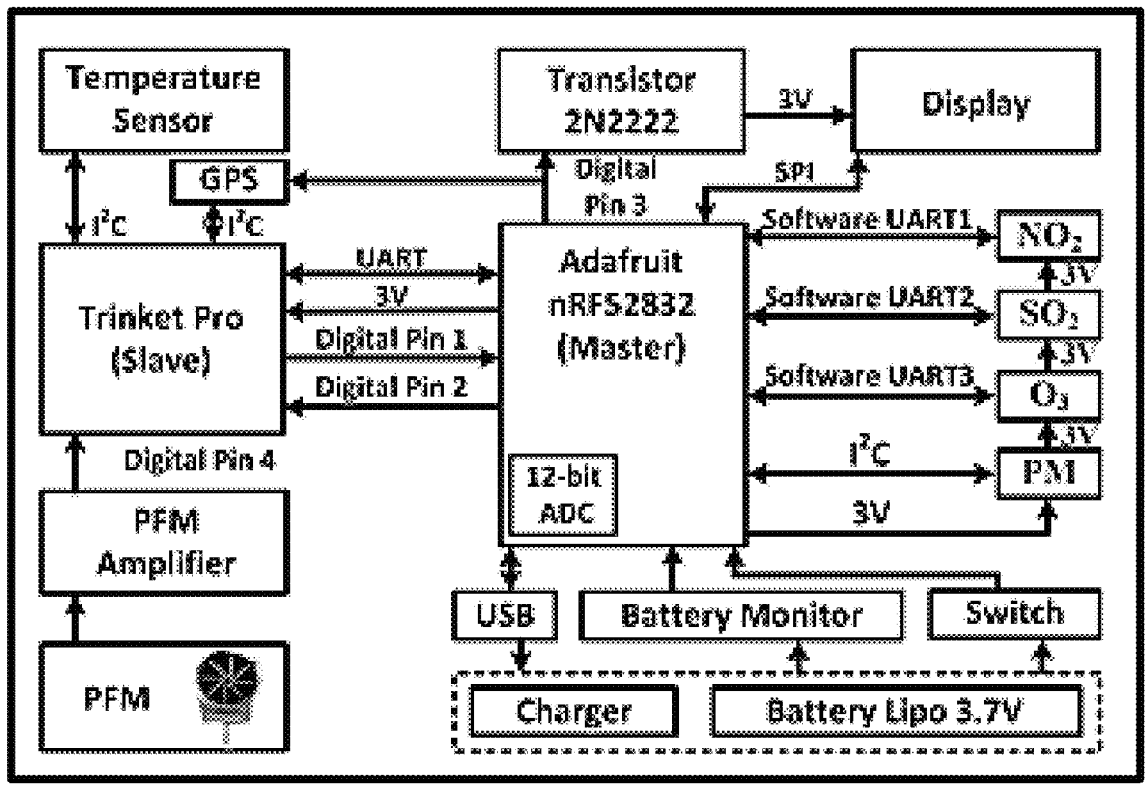
FIG. 2 shows a hardware block diagram of the SCHMT device of FIGS. 1A-1B.

FIG. 1B shows a schematic of an exemplary system of the present disclosure that features the SCHMT device 100. In particular, the left portion of the figure shows a fully assembled SCHMT, where the total casing size of the device is 100 mm L×70 mm W×45 mm H and is printed with 3D PLA (Polylactic acid) material. Physiological parameters and sensor data that are capable of being monitored by the SCHMT device are also shown. The middle portion of the figure shows a person wearing the SCHMT device 100 around his neck (via a cord). The right portion of the figure shows the SCHMT device being communicatively coupled to the wearer's smart phone device and/or computing device such that these devices may be communicatively coupled to medical personnel as shown in the top right portion of the figure. The full hardware block diagram of an exemplary embodiment of the SCHMT device is illustrated in FIG. 2. The overall embedded hardware for the SCHMT is demonstrated in FIG. 3, where a top view of an assembled circuit board for the device is shown on the left and a bottom view of the assembled circuit board is shown on the right.

In various embodiments, an exemplary SCHMT device utilizes two processing boards: an embedded microcontroller (slave) and an embedded microprocessor (master). In an example illustration, the Adafruit nRF52832 acts as an embedded microprocessor. The Adafruit nRF52832 is a high-speed performance microprocessor consisting of Arm® Cortex-M4 CPU with a floating-point unit running at 64 MHz. It encompasses high-speed Bluetooth mesh with Low Power Energy and various communication peripheral features such as I²C, UART, and SPI. Furthermore, the Adafruit nRF52832 is interfaced with different sensors such as PM sensor (I²C), Display (SPI), and Gas Sensors (Software UART). The Trinket Pro is a 3.3V low-power microcontroller with a 12 MHz clocking frequency and 4 KB flash memory. The Trinket Pro is equipped with Push Button (digital pin), PFM amplifier (digital pin), Temperature Sensor (I²C), and GPS (I²C). The data communication between the master processor and slave controller is performed by Serial UART protocol.

Various specifications of SCHMT sensors are summarized in Table I (below). In various embodiments, SPEC electrochemical digital gas sensors are selected for measuring the environmental gases. These sensors have low power consumption (100 μW), good reproducibility, and higher accuracy. The three primary gases are monitored in SCHMT are $SO_2$, $O_3$, and $NO_2$, ranging from 0-10 ppm, 0-20 ppm, and 0-20 ppm, respectively [3SP-SO2-20, 3SP-O3-20, 3SP-NO2-20, SPEC SENSORS LLC]. In addition, these gas sensors also monitor the atmospheric temperature (° F.) and humidity (% RH). The gas sensors are equipped with Analog to Digital Converter (ADC) units. The sensors are interfaced digitally with the master processor via software serial using digital pins shown in FIG. 2. The output of the sensors is generated and measured in the ppb units.

TABLE I

| Sensors | Detection Range | Resolution |
|---|---|---|
| $SO_2$ | 0-10 PPM | 20 PPB |
| $NO_2$ | 0-20 PPM | 50 PPB |
| $O_3$ | 0-20 PPM | 50 PPB |
| PM PMSA003I | 0.3-1.0, 1.0-2.5, 2.5-10 μm | 1 μg/m³ |
| Temperature (MLX9061) | −40° C. to 125° C.-ambient −70° C. to 380° C.-object | 0.02° C. |
| GPS (PA1010D) | N/A | up to 10 locations updates per second |
| PFM | 0-300 KHz | N/A |

In various embodiments, the Adafruit PMSA003I sensor measures the number of particles present in a specific atmosphere with varied sizes. The particulate matter uses laser scattering technology to measure the number of particles with different diameters per unit volume. Furthermore, the Adafruit® PMSA003I sensor measures the particulate matter per 0.1 L air by categorizing it into 0.3 μm, 0.5 μm, 1.0 μm, 2.5 μm, 5 μm, and 10 μm size bins. Master processor reads the sensor data using the I²C protocol shown in FIG. 2. The 3V, 240×240 pixel Adafruit 1.54" TFT display is interfaced with the master processor to improve graphical user interfacing. In various embodiments, the SCHMT device also includes a microSD cardholder to save data and is interfaced with the processor using the SPI communication protocol shown in FIG. 2. In an exemplary embodiment, the SCHMT device uses a 16 GB microSD card to store SCHMT data. The display shows the patient's PFM status, battery voltage, and ambient environment temperature. However, more visual graphic features can be added on display according to patient requirements.

Besides the environmental temperature measurement of the gas sensors, the body temperature and external environmental temperature are measured with the Sparkfun® MLX9061 sensor. Accordingly, in various embodiments, the temperature sensor 140 and an environment temperature sensor 150 can be integrated into a single temperature sensor (e.g., an infrared thermometer sensor). The MLX9061 is a factory calibrated IR thermometer sensor with a range from −70° C. to 380° C. The body temperature is measured by placing a fingertip on top of a sensor pad (that is accessible via a side of the SCHMT device).

Figure 3:
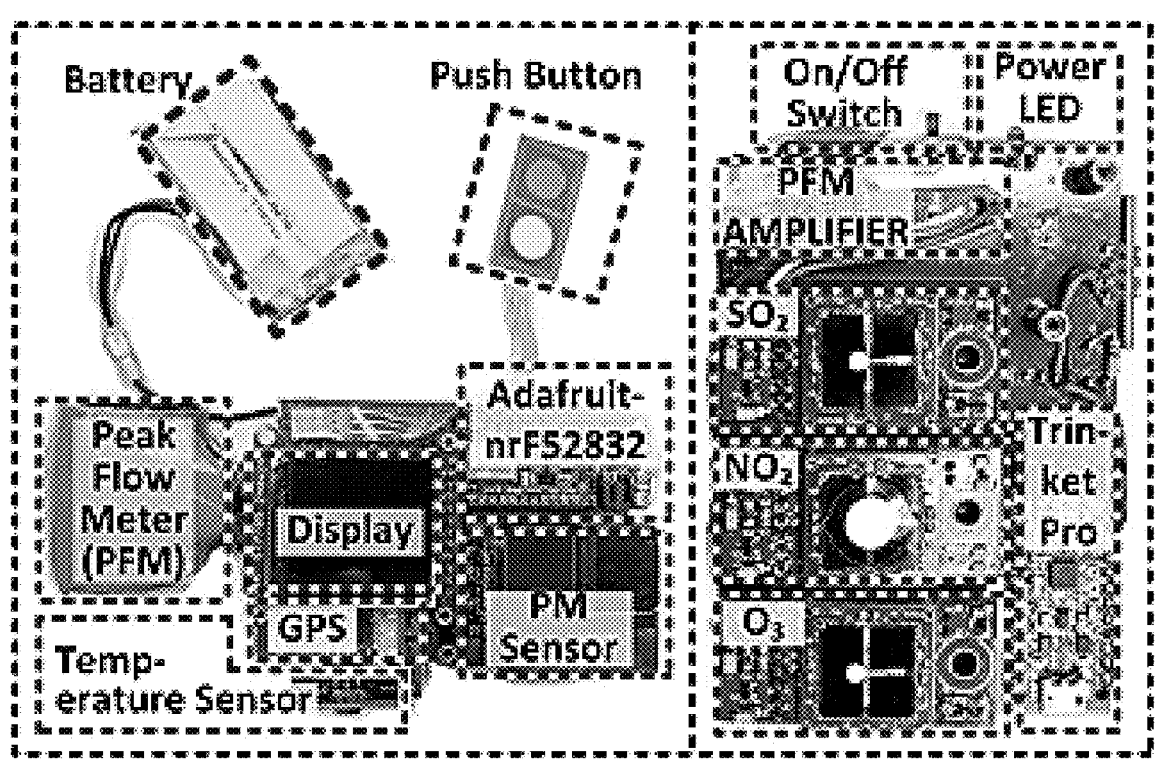
FIG. 3 shows top and bottom views of an assembled circuit board for a prototype of an SCHMT device in accordance with various embodiments of the present disclosure.

The lung performance test of the chronic patient is performed by blowing air into the PFM module, which is shown in FIG. 3. The PFM module generates an ON/OFF pulse train with different duty cycles by rotating a blade between the transmitter and receiver IR sensor. The pulse train is amplified in the PFM amplifier module (74HC14D) and sent to the Trinket Pro digital input pin 4. The PFM unit is modified by adding an IR source to avoid the dependency of the performance of this unit to the light condition. In addition, the body temperature and lung performance tests are performed simultaneously by pressing a push button on a side of the device. The Trinket Pro reads the sensor values using the I²C communication protocol. At the end of the test process, the data are sent to the master processer via the hardware UART bus to be stored in the memory.

In various embodiments, a highly sensitive (−165 dBm) Global Positioning System (GPS) module is integrated with SCHMT to determine hazardous environmental exposure of the user by its precise location detection mechanism. The GPS module is interfaced with Trinket Pro through the $I^2C$ protocol. The user's location is updated every 2 seconds in active mode. The SCHMT uses a 2000 mAh LiPo battery. The battery is rechargeable and can be charged by the embedded charging circuit of the microprocessor. The battery level is monitored by an internal 12-bit ADC, shown in FIG. 2. Additionally, the device is set to a two-run mode alternatively to improve the device's overall run-time efficiency. The device can run up to 48 hours in single charge.

Figure 4:
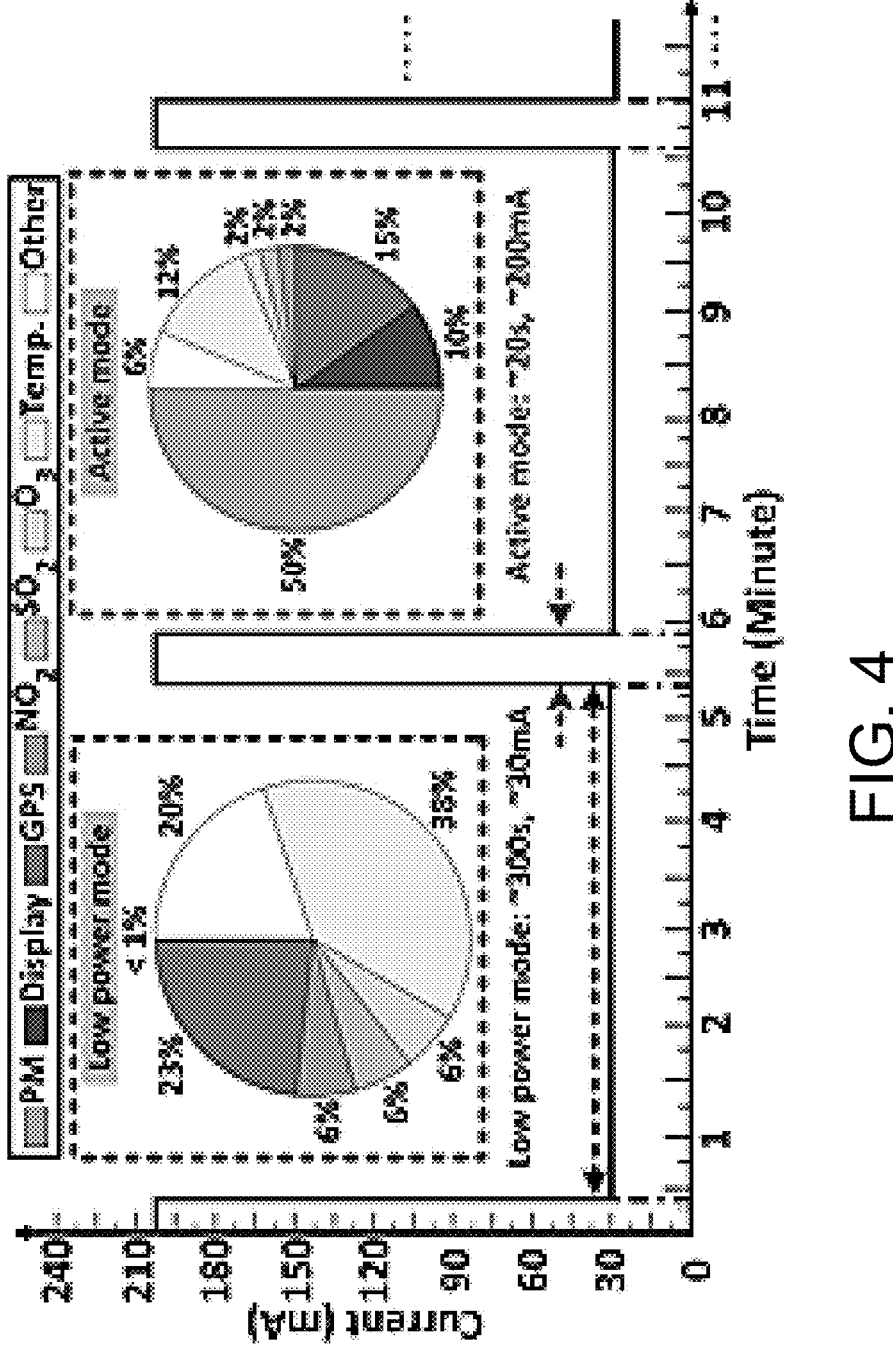
FIG. 4 shows pie charts indicating power consumption levels during active and low mode phases of an exemplary SCHMT device.
Figure 5:
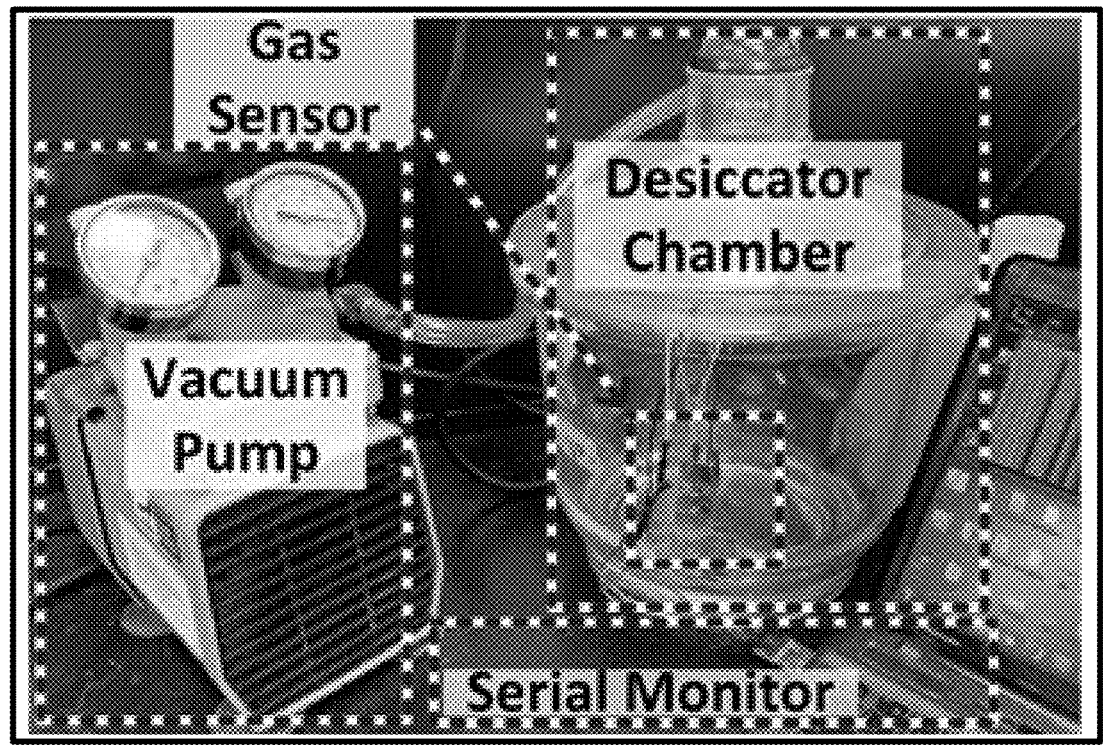
FIG. 5 is a photograph showing an experimental calibration setup of the gas sensors of the SCHMT device.

For evaluation purposes, the power consumption of individual units of the implemented SCHMT are monitored and the results are presented in FIG. 4. Here, the active mode phase has a duration of 20 seconds and consumes 200 mA, while in the low power mode, the device consumes 30 mA for 300 s. During testing, the display, GPS, and PM sensor are set to sleep mode while the device is run in low power mode. However, the display has no sleep-mode pin, so a 2N2222 transistor is used to switch off the display (illustrated in FIG. 2). For evaluation purposes, the performance of all SCHMT sensors was performed individually in different environmental setups to evaluate the robustness of the SCHMT device. FIG. 5 is a photograph of an experimental setup for the gas sensor calibration in clean air. Initially, gas sensors are placed inside the desiccator chamber for at least 1 hour at average room temperature with –0.1 atmosphere pressure. After the initialization period (stabilization), the sensors are calibrated to almost zero with the help of an external UART module connected to the laptop.

Figure 6A:
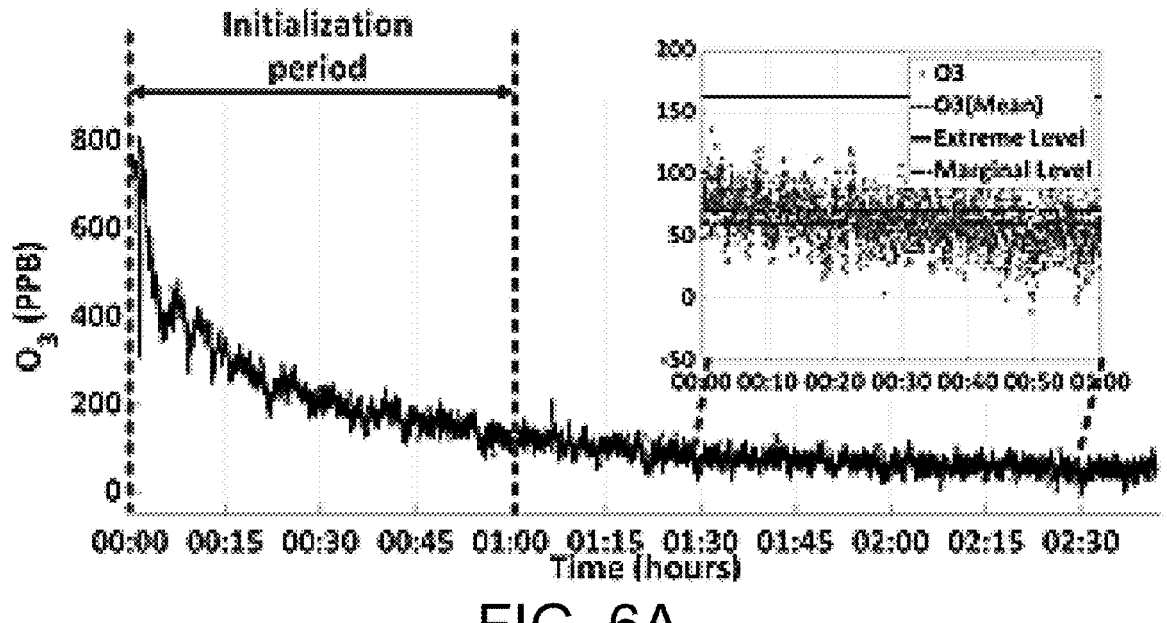
FIGS. 6A-6C show measured results of (A) an ozone gas sensor, slow response rate, (B) nitrogen dioxide gas sensor, rapid response rate, and (C) Sulphur dioxide gas sensor, rapid response rate for an exemplary SCHMT device.
Figure 6B:
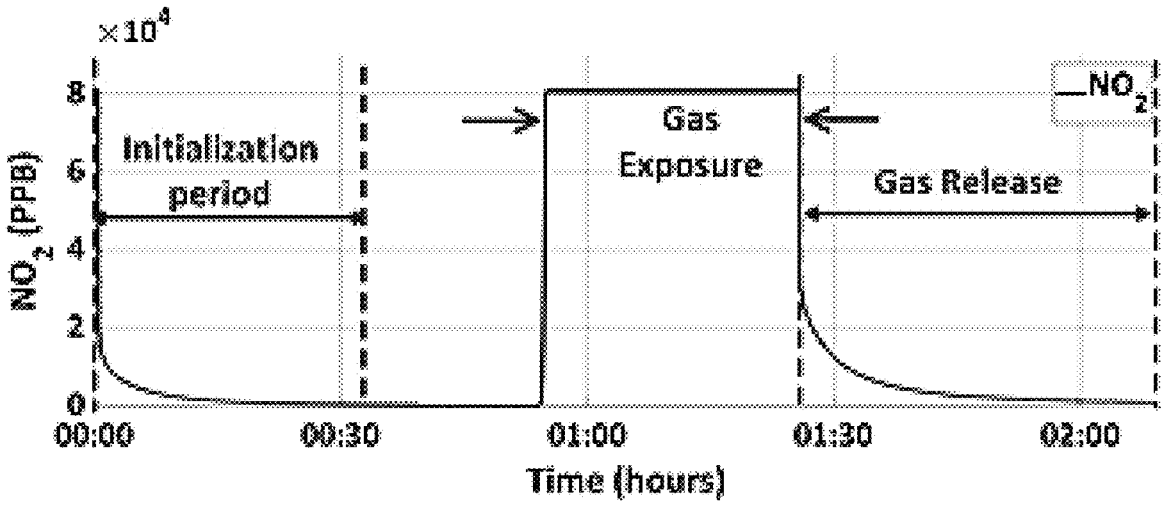
Figure 6C:
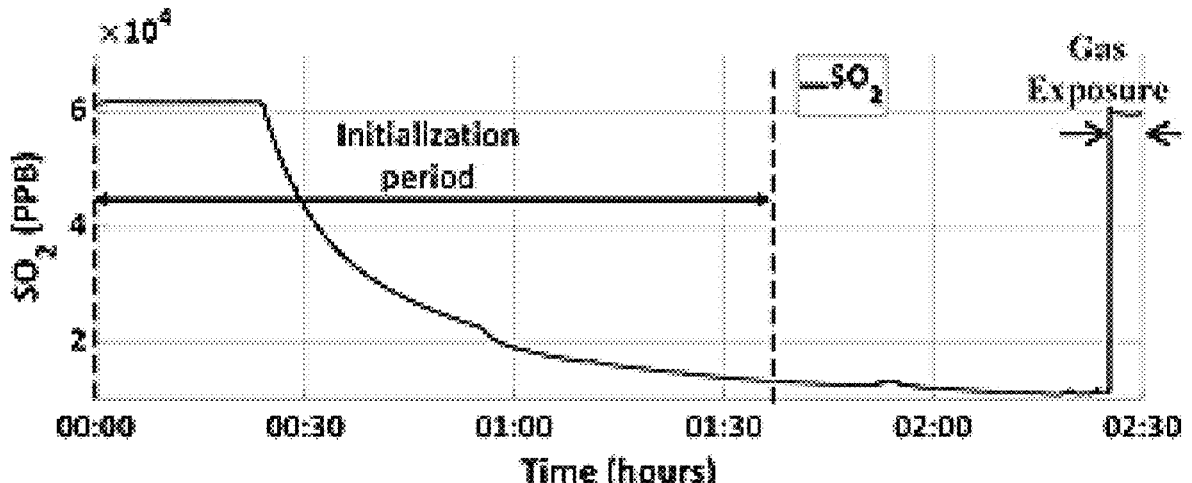
Figure 7A:
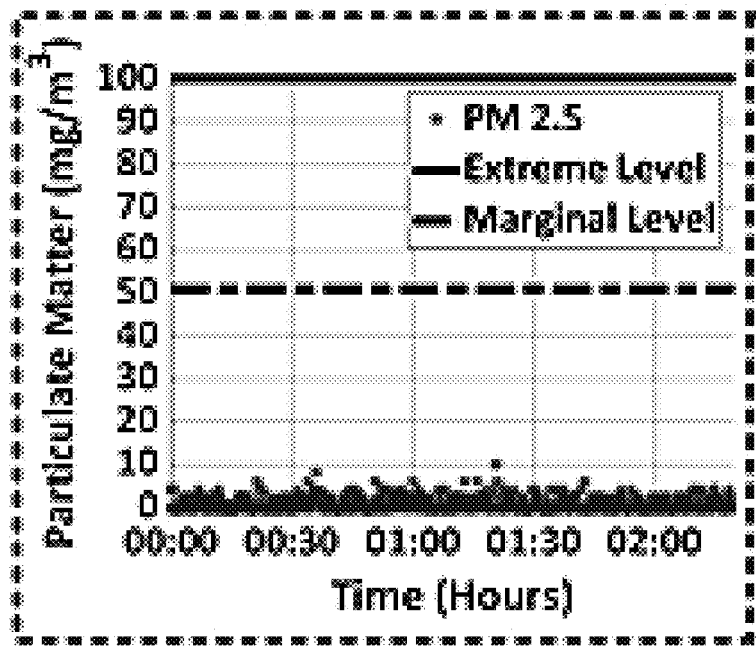
FIGS. 7A-7B show measured results of different size particulate matter present in the environment with air quality levels of (A) PM2.5 and (B) PM10.0.
Figure 7B:
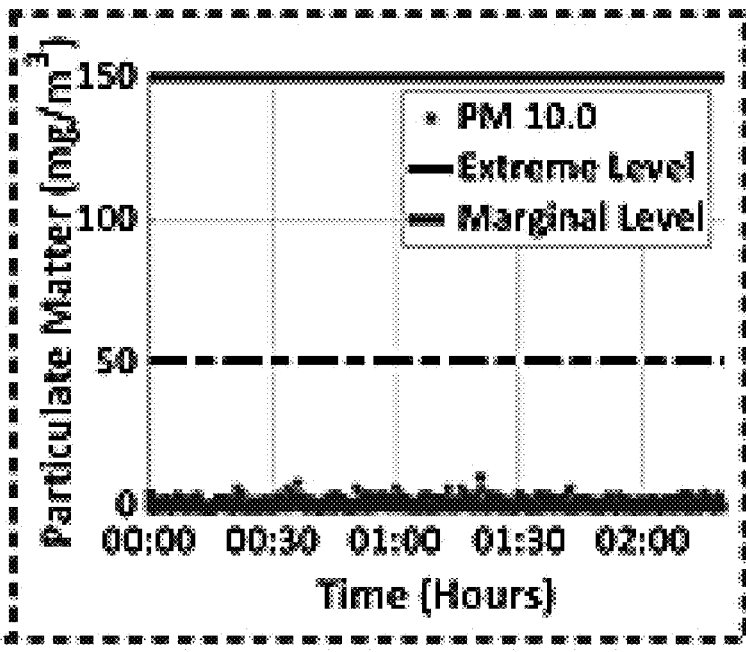

The low response rate experiment was performed on the $O_3$ sensor by placing the sensor in a calibration stochastic environment (FIG. 5). The $O_3$ sensor measured 59.39 PPB mean value after the initialization period, as shown in FIG. 6A. In the inset of FIG. 6A, the minimum, maximum, and average levels of $O_3$ gas) are indicated. To validate the rapid response rate of the gas sensor, we have exposed the $NO_2$ and $SO_2$ sensors with sudden gas exposure. The $NO_2$ and $SO_2$ sensors were placed in the chamber alternatively and were examined by infusing gases in the desiccator chamber. The $NO_2$ and $SO_2$ gases were produced by the chemical reaction of nitric acid (6 ml) with pure copper (4g) and burning Sulphur (3g) in the desiccator chamber, respectively. FIGS. 6B and 6C illustrate the rapid change in the $NO_2$ and $SO_2$ sensor results from the sudden change in gas mass in the chamber.

Figure 8:
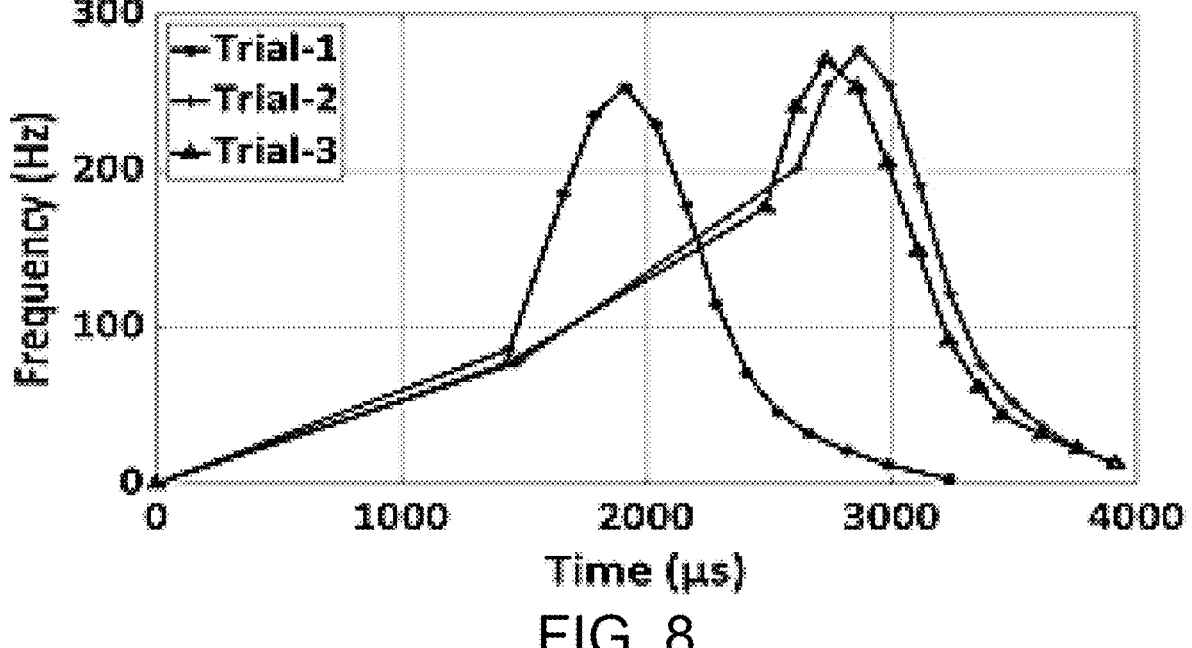
FIG. 8 shows measured results of a peak flow meter (PFM) sensor, indicating the lung performance of three trials of an exemplary SCHMT device.

The SCHMT's PM sensors measure the various size of particulate matter; however, the Local or Federal air quality stations only measures PM2.5 and PM10.0. As a result, only PM2.5 and PM10.0 sensors' values were evaluated by comparing values with the Birmingham Air Quality Station, shown in FIGS. 7A-7B. Moreover, FIGS. 6A-6C, 7A, and 7B illustrate the marginal and extreme air quality levels for individuals obtained from the Environmental Protection Agency (EPA) organization. Additionally, three lung performance trials were performed via the PFM module 110. The output of the PFM was measured and illustrated in FIG. 8, ranged from 215 to 300 Hz.

Figure 9A:
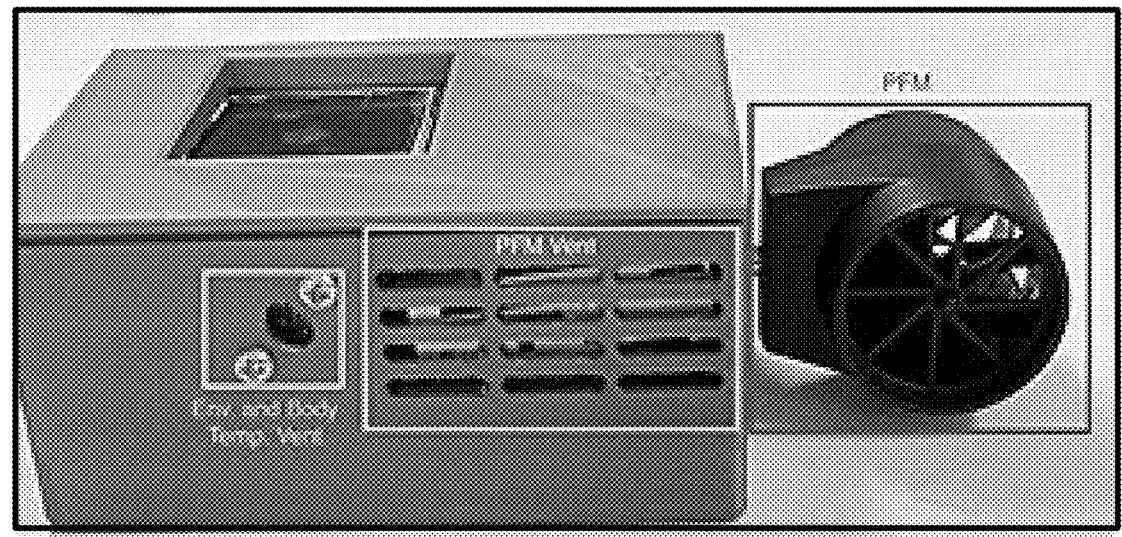
FIGS. 9A-9E shows photographs of side and front views of a prototype of the SCHMT device.
Figure 9A:
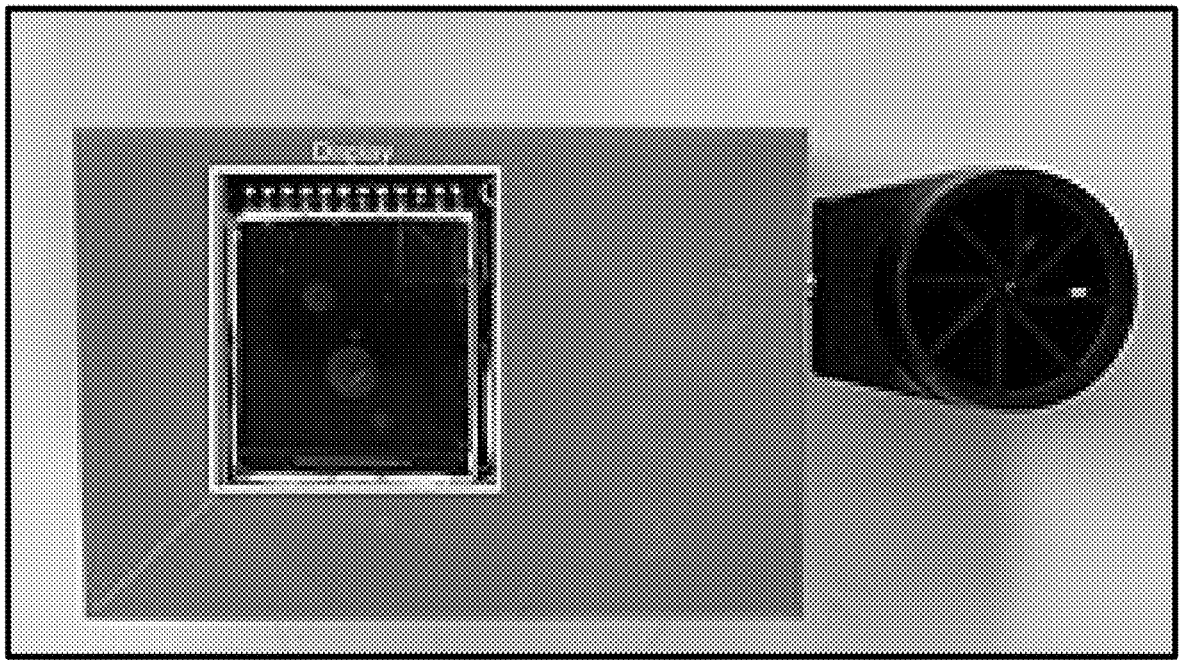
Figure 9B:
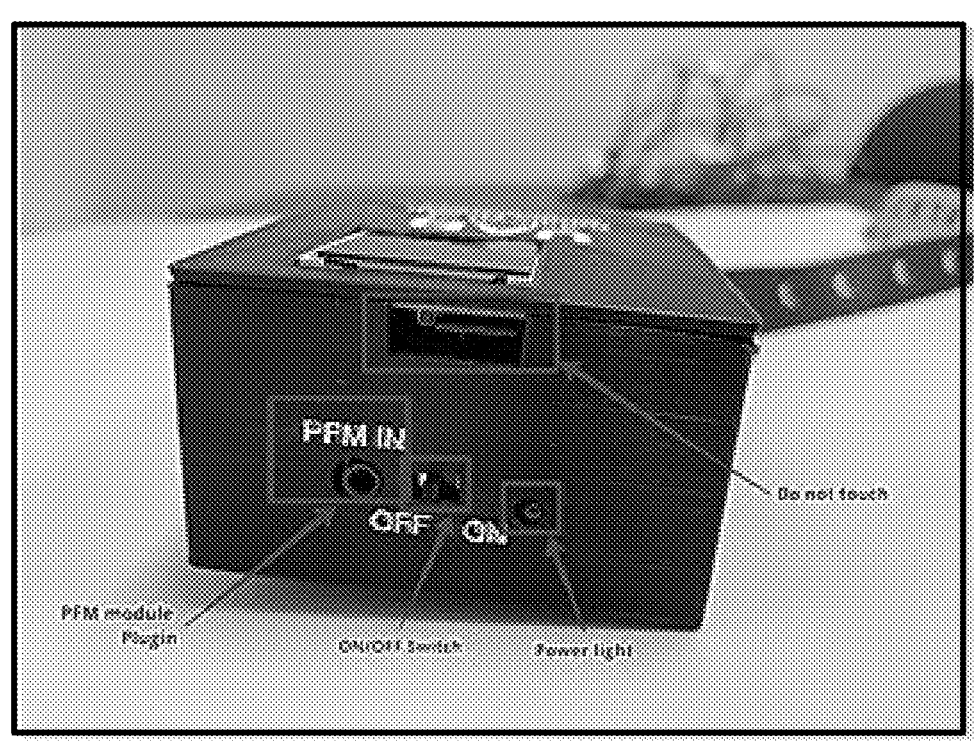
Figure 9C:
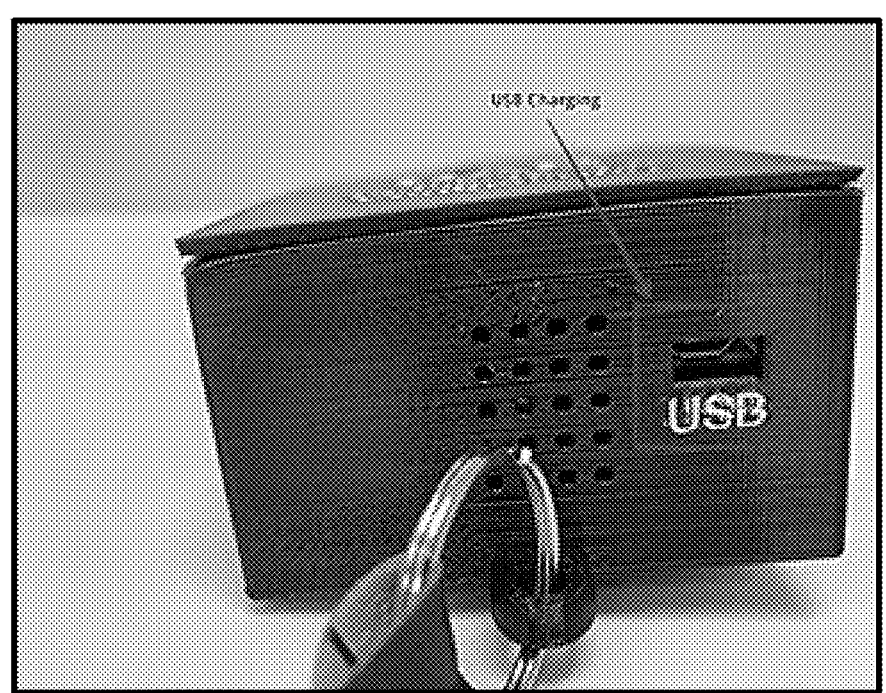

Next, FIGS. 9A-9E show photographs of side and front views of a prototype of the SCHMT device, with FIGS. 9A and 9C showing air vents that allow for reading various air quality levels. In accordance with the present disclosure, the prototype device allows for daily (or other user-defined interval) measurement of environmental condition at individual level and range of exposure for particular matter concentration, $NO_2$, $SO_2$, and $O_3$, temperature, blood oxygen level and relative humidity. It also measures for pulmonary functions using a peak flow meter (PFM) and movement (speed) tracker that allows real-time spatial-temporal resolution data collection in relation to individual GPS coordinates, with activity parameter for precise sampling intervals.

The device has Wi-Fi and Bluetooth capability allowing the readings to be instantly transferred via the Wi-Fi network and a user's smart phone to a central unit (e.g., at the (UAB) Pulmonary clinic) for real time daily assessment. For this capacity, a configurable multi-layer PCB has been developed to include a processor unit (microprocessor), data transceiver unit, and sensor interface electronics. To transfer data between the SCHMT device and a central unit, the user's smart phone and Bluetooth Low Energy (BLE) technology can be utilized. In various embodiments, the SCHMT device is configured for short and long ranges data transmission network to guarantee 24/7 of air quality monitoring.

The broadcasted data can be viewed by the health care professionals/clinic for monitoring individual status and exacerbation of COPD, symptoms, and daily medication adjustment/advice. As such, the SCHMT device can provide doctors with the full story of patient daily exposure, enabling them to identify patients' thresholds and triggers that have previously been unknown. In accordance with the present disclosure, the SCHMT device is small in size and light enough to be worn by participants during daily tasks and not interfere with normal activities.

Figure 9D:
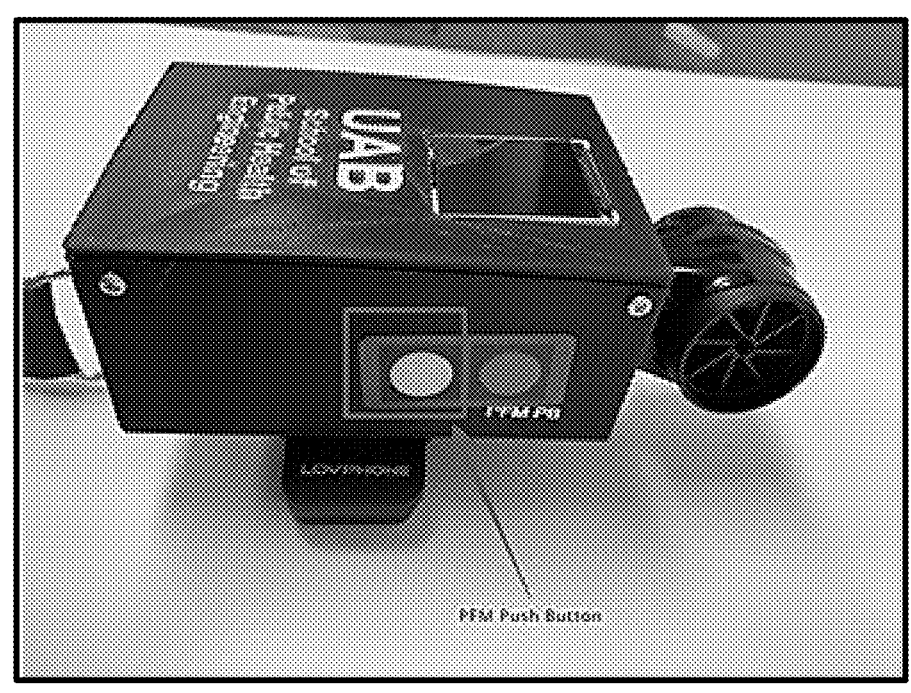
Figure 9E:

To demonstrate select operations, an exemplary SCHMT device can be turned On and Off by using the Off/On switch shown in FIG. 9B. To measure air flow and body temperature, a user can take a temperature reading while measuring their lung pressure by placing his or her finger on a temperature sensor pad while pressing a separate peak flow meter (PFM) button (as shown in FIGS. 9D-9E) and taking a deep breath for measurement. Thus, PFM and body temperature reading can be taken simultaneously. To charge a local battery of the SCHMT device, the display can first indicate if the battery is in need of charging, and if so, a charging port (see FIG. 9C) can be used to charge the local battery.

In brief, a Smart Chronic Health Monitoring Tool (SCHMT) device is provided to monitor the real-time ambient environment of individuals. The SCHMT device can detect and identify the worsening or severity of an individual's diseases after exposure to a harmful environment. The SCHMT device outperforms other methods by measuring $NO_2$, $SO_2$, $O_3$, PM, humidity, PFM, geographic location, body temperature, and environmental temperature for any given indoor or outdoor setting. The SCHMT is a small affordable wearable device with internal data logging system. However, in various embodiments, local data management can be converted to a cloud-based system.

In various implementations, application of the SCHMT device can focus on patients with COPD and Asthma disease from all ages and as young as 40-65 years old. Additionally, applications can be expanded to patients and any individual with compromised respiratory conditions as well as Covid-19 and other variant patients who can be monitored from home, which will allow for Covid-19 and other patients to be observed during and after hospitalizations for close monitoring on daily (or other user-defined interval) basis for their respiratory functions and heart. As such, this innovative technology can be used and adapted by various hospitals, health care providers, and insurance companies at local and regional level and will allow for increase in in-patient and out-patient monitoring for exposure and respiratory factors, thereby enabling patients to make personal health and lifestyle related changes like routes to travel, blocks and hours of the day to avoid, and areas to live in.

This technology will not only improve patients and chronic care for users through continuous assessment and daily monitoring of patients' exposure, triggers, and respiratory function, but also to allow users to monitor their health and eliminate the environmental exposure effects on their health; learning their triggers and when to seek emergency care and adjust medications. This will be a major leap toward connected health and personalized medicine, such that each patient can be studied individually and triggers and thresholds can be assigned based on their health conditions.

Figure 10:
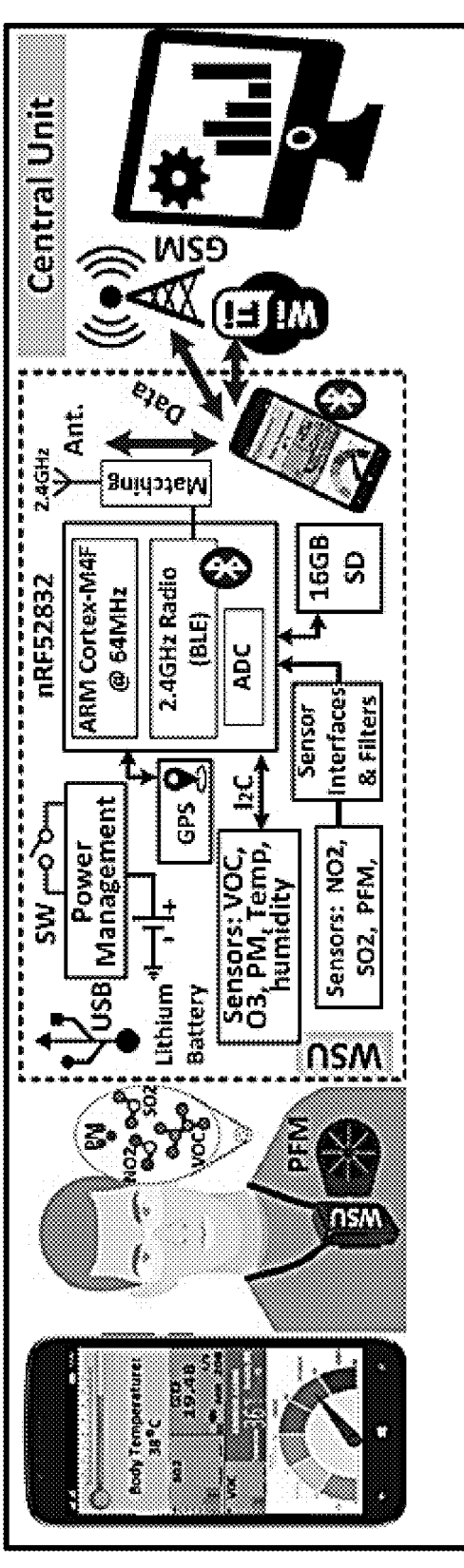
FIG. 10 shows block diagram of an exemplary system containing the SCHMT device in accordance with various embodiments of the present disclosure.

In accordance with various embodiments, the SCHMT device and its configurations allow for real-time monitoring of patient's daily exposure, body temperature, blood oxygen level and lung capacity through an integrated peak flow meter (PFM). The SCHMT device enables patient to have access to their daily exposure and their health condition while data is communicated to health care providers and patient's doctor. An exemplary SCHMT device collects sensor data and displays associated information on the unit itself and wirelessly sends the sensor data to a main portal site. The SCHMT device includes (1) battery and power management unit, (2) processor and controller units, (3) Global Positioning System (GPS) and data storage (e.g., 16 GB), and (4) data transceiver units (e.g., Bluetooth Low Energy, Wi-Fi, and Global System for Mobiles (GSM) units), and (5) sensor units along with their interface circuits. FIG. 10 shows a top-level block diagram of an exemplary system containing the SCHMT device, smart phone interface, and a central unit (having a main portal site). In various embodiments, the system also features a data collection application that has been developed for smart phone and Graphical User Interfaces (GUI) for the central unit. This allows patients to view and monitor their daily exposure outdoor and indoor in real-time while communicating with their health care provider.

Figure 11:
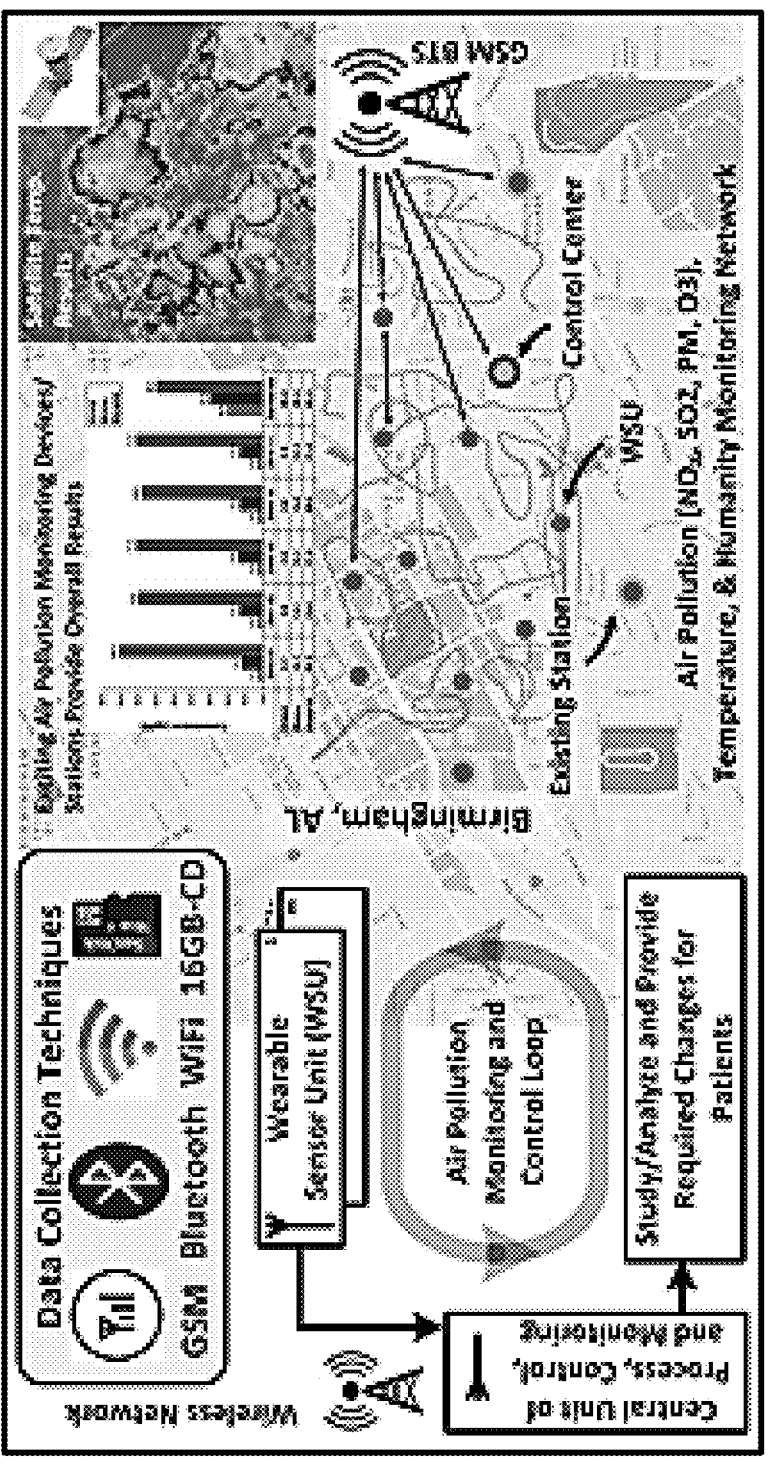
FIG. 11 shows a system diagram of the SCHMT device collecting sensor data and providing the data to the central unit for developing an air pollution map.

For example, FIG. 11 shows a system diagram of the SCHMT device ('wearable sensor unit (WSU)") collecting sensor data and providing the data to the central unit. And, specifications of an exemplary SCHMT device (WSU), including individual modules and components, are presented in FIG. 12. Accordingly, the central unit can collect data from multiple SCHMT devices for an extended period of time (e.g., 24/7). In various embodiments, the collected data is initially stored in the an SD Card at the SCHMT device and delivered to the smart phone via Bluetooth Low Energy (BLE) daily or any other user-defined period. The central unit uses the network to collect the data (e.g., sensor data, GPS data, etc.) from SCHMT devices by sending the operator's requests to the smart phones associated with multiple SCHMT devices. In various embodiments, an exemplary system can cover a large area and can develop an air pollution map with high-resolution (regarding the location) based on the users' locations (as provided via GPS location data). Additionally, the SCHMT device can collect body temperature and lung capacity data through a peak flow meter (PFM) (integrated with the SCHMT device), a significant indicator for patients with lung diseases.

In accordance with embodiments of the present disclosure, the central unit can utilize GPS and mapping software to enhance monitoring capabilities through the SCHMT device's precise location-tracking which allows for real-time monitoring of the user/device location. The aforementioned mapping software allows for the visual representation and analysis of the user's location data. For example, the central unit can be configured to visually represent a user/ device's current location on a map interface and allows for reviewing past routes, movement, patterns, and trends in the device location history. The combination of GPS data and environmental sensor data allows for a comprehensive understanding of environmental conditions in different locations through its mapping system. Thus, the GPS and mapping features can contribute to personal safety and security in emergency situations or in industries with remote workers by providing real-time location information for timely response and assistance.

One or more or more of the components described herein that includes software or program instructions can be embodied in any non-transitory computer-readable medium for use by or in connection with an instruction execution system such as a processor in a computer system or other system. The computer-readable medium can contain, store, or maintain the software or program instructions for use by or in connection with the instruction execution system.

The computer-readable medium can include physical media, such as, magnetic, optical, semiconductor, or other suitable media. Examples of a suitable computer-readable media include, but are not limited to, solid-state drives, magnetic drives, flash memory. Further, any logic or component described herein can be implemented and structured in a variety of ways. One or more components described can be implemented as modules or components of a single application. Further, one or more components described herein can be executed in one computing device or by using multiple computing devices.

Thus, apparatuses, systems, and methods of the present disclosure are configured and enabled to assess respiratory functions and transfer data in real-time to healthcare providers for early intervention, patient management, and medication adjustment. The foregoing enables physicians to receive alerts for high readings and identify at-risk patients for quick action, improving medical decision-making, while also empowering patients to make healthier lifestyle choices.

In an exemplary wearable sensor device (Smart Chronic Health Monitoring Tool) of the present disclosure provides passive monitoring, prompt data access, and alerts for emergency assessments and medication adjustment. With Bluetooth capability, GPS, and a movement/speed tracker, the wearable sensor device can monitor physiological, behavioral, and environmental parameters. Such a wearable sensor device can also communicate data on patient's environmental exposure and physiological status to their healthcare provider, facilitating improved care and reducing exacerbations and emergency hospitalizations. It also enables communication between physicians and patients.

Thus, an exemplary wearable sensor device of the present disclosure provides continuous real-time monitoring of users' health and exposure status, connecting the information with healthcare providers for early intervention. Physicians can gain insights into patients' daily exposure, identifying thresholds and triggers previously unidentified. The data collection application can notify, track, and manage early signs of worsening COPD/Asthma, displaying maps with high pollutant concentrations for better health and behavioral control and can facilitate one-on-one care between patients and healthcare providers from the comfort of their homes.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Therefore, at least the following is claimed:

1. A wearable sensor device comprising:
a processor;
a plurality of gas sensors integrated on the wearable sensor device, wherein the gas sensors measure an amount of $NO_2$, $SO_2$, and $O_3$ present in ambient air;
a peak flow meter sensor integrated on the wearable sensor device;
a temperature sensor integrated on the wearable sensor device;
a GPS sensor integrated on the wearable sensor device;
one or more transceivers integrated on the wearable sensor device;
an electronic display; and
wherein the processor is coupled to the electronic display and is operable to display sensor data measured from the wearable sensor device.

2. The wearable sensor device of claim 1, further comprising a particular matter sensor integrated on the wearable sensor device.

3. The wearable sensor device of claim 2, wherein the particulate matter sensor categorizes a size of particulate matter as belonging to one of 0.3 μm, 0.5 μm, 1.0 μm, 2.5 μm, 5 μm, and 10 μm size bins.

4. The wearable sensor device of claim 1, wherein the temperature sensor is operable to measure a temperature of ambient air in addition to a body temperature of a wearer.

5. The wearable sensor device of claim 4, wherein the temperature sensor comprises a sensor pad that is operable to be pressed by a finger of the wearer in order to measure the body temperature of the wearer.

6. The wearable sensor device of claim 1, wherein the one or more transceivers are operable to communicate sensor data measured from the wearable sensor device to a computing device.

7. The wearable sensor device of claim 6, wherein the computing device comprises a smart phone or personal computer.

8. The wearable sensor device of claim 1, wherein the gas sensors measure a humidity level of ambient air.

9. The wearable sensor device of claim 1, wherein the processor is operable to perform a body temperature measurement using the temperature sensor simultaneously with performing a lung performance measurement using the peak flow meter sensor.

10. A method comprising:
collecting, by a wearable sensor device to worn by a user, sensor data from each of a plurality of gas sensors integrated on the wearable sensor device, wherein the gas sensors measure an amount of NO2, SO2, and O3 present in ambient air; a peak flow meter sensor integrated on the wearable sensor device; a temperature sensor integrated on the wearable sensor device; and a GPS sensor integrated on the wearable sensor device; and
displaying, by an electronic display of the wearable sensor device, sensor data measured from the wearable sensor device.

11. The method of claim 10, wherein the sensor data is further collected from a particular matter sensor integrated on the wearable sensor device.

12. The method of claim 11, wherein the particulate matter sensor categorizes a size of particulate matter as belonging to one of 0.3 μm, 0.5 μm, 1.0 μm, 2.5 μm, 5 μm, and 10 μm size bins.

13. The method of claim 10, wherein the sensor data collected from the temperature sensor includes a temperature of ambient air in addition to a body temperature of a wearer.

14. The method of claim 13, wherein the temperature sensor comprises a sensor pad that is operable to be pressed by a finger of the wearer in order to measure the body temperature of the wearer.

15. The method of claim 10, further comprising communicating sensor data measured from the wearable sensor device to a computing device.

16. The method of claim 15, wherein the computing device comprises a smart phone.

17. The method of claim 10, wherein the gas sensors measure a humidity level of ambient air.

18. The method of claim 10, wherein the sensor data comprises a body temperature measurement using the temperature sensor and a lung performance measurement using the peak flow meter sensor, wherein the method comprises performing the body temperature measurement simultaneously with performing the lung performance measurement using the wearable sensor device.

19. The method of claim 18, wherein the wearable sensor device includes a temperature sensor pad and a peak flow meter button, wherein the temperature sensor pad is pressed using a finger of the user to measure a body temperature of the user at a same time as the user presses the peak flow meter button to measure a lung performance of the user.

20. The wearable sensor device of claim 1, wherein the wearable sensor device includes a temperature sensor pad and a peak flow meter button, wherein the temperature sensor pad is operable to be pressed using a finger of a wearer of the wearable sensor device to measure a body temperature of the wearer at a same time as the wearer presses the peak flow meter button to measure a lung performance of the wearer.

* * * * *